United States Patent [19]

Harder et al.

[11] Patent Number: 4,798,792

[45] Date of Patent: Jan. 17, 1989

[54] BACTERIAL HYDROXYLATION OF CODEINE

[75] Inventors: Patricia A. Harder; Daniel A. Kunz, both of Wilmington, Del.

[73] Assignee: E. I. Du Pont de Nemours and Company, Wilmington, Del.

[21] Appl. No.: 774,026

[22] Filed: Sep. 9, 1985

[51] Int. Cl.⁴ ............................................. C12P 17/18
[52] U.S. Cl. .................................. 435/119; 435/886; 435/897; 435/900; 514/282; 546/44
[58] Field of Search ....................... 435/119, 118, 897; 514/282; 546/44

[56] References Cited

PUBLICATIONS

Tsuda et al., Microbial Transformation of Steroids and Alkaoids, 167–193, 1964.
Yamada et al., *Chemical and Pharmaceutical Bulletin* 10, 981–984, 1962.
Gröger et al., *Experentia* 25, 95–96, 1969.
Liras et al., *Developments in Industrial Microbiology*, 16, 401–405–1975.
Liras et al., *Applied Microbiology*, 30, 650–656, 1975.
Sewell et al., *Applied Microbial Biotechnology*, 19, 247–251, 1984.
Rozza et al., *Journal of Medicinal Chemistry*, 18, 791–794, 1975.
Kunz, D. A., Abstracts of the Annual Meeting of the American Society of Microbiology, p. 247, Feb. 25, 1985.

*Primary Examiner*—Thomas G. Wiseman
*Assistant Examiner*—Charles L. Patterson, Jr.

[57] ABSTRACT

A microbial process for converting codeine to 14-hydroxycodeine is provided. This process comprises aerobically culturing codeine with bacteria of the genus Streptomyces for at least about 3 days in a rich medium such as soybean flour medium.

15 Claims, 1 Drawing Sheet

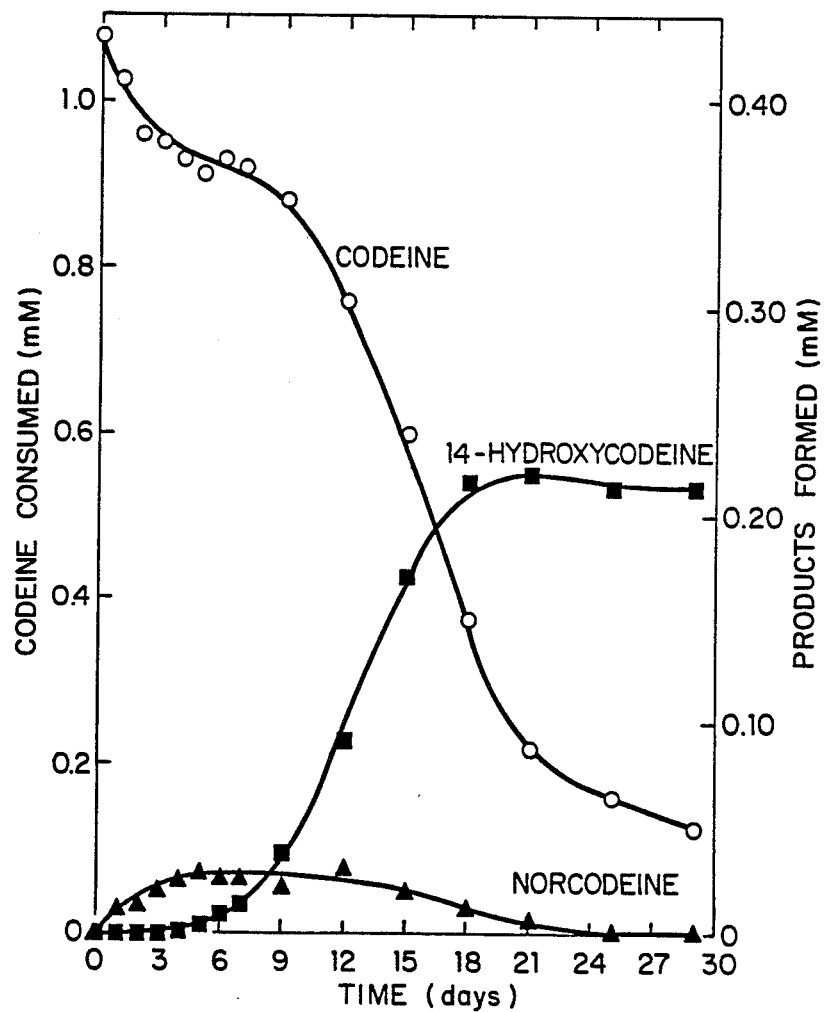

BACTERIAL HYDROXYLATION OF CODEINE

BACKGROUND OF THE INVENTION

1. Field of the Invention

This invention relates to microbial processes for converting codeine to 14-hydroxycodeine and more particularly to such processes by means of culturing codeine with bacteria of the genus Streptomyces.

2. Prior Art

Codeine, morphine, and thebaine are natural alkaloid products of the opium poppy, *Papaver somniferum*. Thebaine is used to prepare a number of commercially important narcotic antagonists and agonist/antagonist analgesics by its chemical modification. Use of codeine and morphine as starting materials is also desirable but appropriate chemical routes for their use have not yet been perfected. A major requirement for the use of these three opium alkaloids for the production of some analgesics and/or narcotic antagonists is the addition of a hydroxyl group in the C-14 position. The present invention provides the first known microbial process for converting codeine to 14-hydroxycodeine with yields and efficiencies of conversion to make the process commercially feasible.

Microbial conversions of alkaloids has been known for about 25 years. Tsuda et al., Microbial Transformation of Steroids and Alkaloids, 167–193, 1964, in the publication of the I. A. M. symposium on Microbiology, Institute of Applied Microbiology. (no. 6), University of Tokyo, disclose that 120 thebaine converting strains were selected from 1700 different bacterial and fungal strains tested for that ability. Most of the 120 strains were from the basidiomycetes, especially from the wood rot fungi *Trametes sanguinea*. Conversions of thebaine to 14-hydroxycodeinone and 14-hydroxycodeine were disclosed. Yields of the products depended on the nutrient solution used for cultivation of the organisms.

Yamada et al., *Chemical and Pharmaceutical Bulletin* 10, 981–984, 1962, disclose that *Trametes sanguinea* was unable to convert morphine or codeine to identifiable oxidation products.

Groger et al., *Experentia* 25, 95–96, 1969, disclose that most of 35 strains of Trametes of European origin could convert thebaine to 14-hydroxycodeinone and various other products. Detailed accounting was not disclosed; however, 14-hydroxycodeine was found only occasionally, in trace amounts.

Liras et al., *Developments in Industrial Microbiology*, 16, 401–405, 1975 disclose the transformation of morphine and codeine by bacteria of the genus Arthrobacter. Morphine was transformed to 14-hydroxymorphine and an unidentified product. Codeine also was transformed into two products, the minor component of which was codeinone. The major transformed product was not identified but it was not 14-hydroxycodeine, 14-hydroxycodeinone, 14-hydroxydihydrocodeinone, or norcodeine.

Liras et al., *Applied Microbiology*, 30, 650–656, 1975, disclose bacterial enzyme preparations from *Pseudomonas testosteroni* which transformed morphine in relatively low yield to 14-hydroxymorphinone and an unidentified product. The enzyme preparations converted codeine to codeinone and 14-hydroxycodeinone.

Sewell et al., *Applied Microbial Biotechnology*, 19, 247–251, 1984, disclose that two species of Streptomyces and several strains of the fungus Cunninghamella transformed codeine by N-demethylating the N-methylpiperidine moiety.

Rosazza et al., *Journal of Medicinal Chemistry*, 18, 791–794, 1975, disclose two species of Streptomyces and several other types of microorganisms that selectively cleave either the 10-methoxy or the 11-methoxy ether groups from 10,11-dimethoxyaporphine. Soybean meal was used for the cultivation of these organisms.

Kunz, D. A., Abstracts of the Annual Meeting of the American Society of Microbiology, page 247, Feb. 25, 1985, discloses that *Streptomyces griseus* ATCC 10137 could catalyze a 4% molar conversion of codeine into 14-hydroxycodeine and norcodeine.

SUMMARY OF THE INVENTION

According to the present invention, provided is a microbial process for preparing 14-hydroxycodeine which comprises contacting codeine, or a water-soluble salt thereof, with bacteria of the genus Streptomyces for a period of at least about 3 days while said bacteria are being aerobically cultured in a rich medium; and recovering 14-hydroxycodeine from the medium.

When the medium is enriched with soybeam flour and when codeine is present in concentrations less than about 5 mM or preferably less than about 2.5 mM, 14-hydroxycodeine is preferentially produced in good yield. It is preferred that cultivation be carried out for a period of about 3 to 30 days, preferably about 10 to 20 days.

BRIEF DESCRIPTION OF THE DRAWING

The drawing is a graph showing the results from Example 13.

DETAILED DESCRIPTION OF THE INVENTION

The following is a list of the bacteria which transform codeine along with their source:

S. griseus: NRRL B8090
S. griseus: ATCC 10137
S. griseus: ATCC 23337
S. griseus: ATCC 13968
S. griseus: ATCC 21897
S. griseolus: ATCC 3325
S. griseolus: ATCC 11796
S. punipalus: NRRL 3529
S. lincolnensis: ATCC 25466
S. species: WH 110

NRRL =Northern Regional Research Laboratory, ATCC =American Type Culture Collection, WH =Woods Hole Collection.

The preferred bacteria derive from *Streptomyces griseus* that are on deposit in the Northern Regional Research Laboratory with accession number NRRL B8090. These bacteria are preferred because they convert codeine efficiency and in good yield, and produce a lower amount of norcodeine or other conversion products. Of course, if larger amounts of norcodeine are desired, one of the other strains of S. griseus can be used in an appropriate rich medium.

The bacteria are cultured and the biotransformation process carried out in a rich medium. A rich medium is well known to those skilled in the art. In general it means that all growth nutrients (e.g. carbon, nitrogen, and the energy source plus growth factors) are supplied in excess with the exact chemical composition being unknown.

COMPOSITION OF BACTERIAL MEDIA

The following is a list of preferred bacterial rich media and the compositions thereof:

Soybean Flour Medium (SFM):
Yeast extract: 5 g/L
Soybean flour: 5 g/L
$K_2HPO_4$: 5 g/L
NaCl: 5 g/L
Glycerol: 20 g/L
Deionized water: 1 L
pH 6.8 (adjusted with 5N HCl)

Yeast Malt-extract Medium (YM):
Yeast extract: 3 g/L
Malt extract: 3 g/L
Bacto-Peptone: 5 g/L
Bacto-Dextrose: 10 g/L
Deionized water: 1 L
pH 6.1 (adjusted with 5N HCl)

Yeast Malt-extract Medium with l-tyrosine (YMT):
YM
L-tyrosine: 2-5 mM
pH 6.1 (adjusted with 5N HCl)

Sporulation Medium (SpB):
Yeast extract: 1 g/L
Beef extract: 1 g/L
Tryptose: 2 g/L
Glucose: 10 g/L
$FeSO_4$: 0.05 g/L
Deionized water: 1 L
pH 7.2 (adjusted with 5N HCl).

Bacto-Agar can be added to the above media in the concentration of 20 g/L to make YM or SpB agar and is used for culture maintenance. All media are sterilized prior to inoculation with bacteria by using conventional procedure, such as autoclaving them for 20 minutes at about 120° C.

Of the above, soybean flour medium is preferred because it gives better yields of 14-hydroxycodeine.

The 14-hydroxycodeine product is recovered from the medium using conventional techniques. Such techniques include extraction into an organic solvent and purification by column chromatography.

14-Hydroxycodeine is an intermediate which can be useful in preparing the commercial pharmaceutical compounds naltrexone, naloxone, oxycodone, nalbuphine, and oxymorphine. For example, 14-hydroxycodeine can be converted to oxycodone by reduction of the 7,8 double bond and oxidation of the 6-αhydroxy group to the ketone.

BACTERIAL CULTURE CONDITIONS

Bacteria were subcultured from stock cultures which were kept frozen at −65° C. in medium containing 8 percent dimethylsulfoxide, or from stock cultures stored at 4° C. on YM or SpB agar slants.

To prepare first stage cultures, a loopful—using an inoculating needle—of bacterial cells was inoculated into 5 mL of SpB and grown for 24 to 72 h at 30° C. The first stage cultures were shaken at 250 rpm on a gyratory shaker during their incubation. All cultures were so shaken to provide appropriate aeration which is important for the growth of these organisms.

Generally, a 2.5 mL aliquot from the first stage culture just described was then added to 100 mL (or a 1.25 mL aliquot to 50 mL) of rich medium such as SFM, YM, or YMT contained in a 500 mL Erlenmeyer flask. Cultures containing 500 mL of a bacterial suspension were grown in a 2L flask in some experiments. Prior to sterilization, the pH of the medium was adjusted to between pH 6.0 and pH 7.0. Thereafter, no effort was made to control or adjust the pH which in some cases increases to nearly 9.0. There was little difference in the yields of 14-hydroxycodeine whether the bacterial transformation occured in YM or YMT medium. Because increased yields of 14-hydroxycodeine without concomitant increased yields of norcodeine, were obtained in SFM, it is the preferred medium for carrying out the process.

The resulting culture was grown for 18-24 h on a gyratory shaker, then a solution of sterile codeine phosphate was added to a final concentration of 1mM (0.29 mg/mL). Other water-soluble salts of codeine such as codeine hydrochloride of codeine acetate can also be used. After the addition of the codeine salt, the resulting culture was incubated, with constant shaking, for up to 30 days. The temperature of incubation is not critical but it should generally be under about 32° C., preferably in the range of 25° to 30° C. Samples (10 mL) were withdrawn at varying intervals and analyzed for 14-hydroxycodeine and norcodeine as described below.

DETECTION OF CODEINE, 14-HYDROXYCODEINE AND NORCODEINE

1. Analysis by gas chromatography (GC):

Culture samples (10 mL) were centrifuged at 8,000 x g and resulting supernatant fluids were brought to a pH of 9.5, and twice extracted with an equal volume of a 2:1 mixture of methylene chloride/ethyl alcohol. The resulting organic phase was separated from the water and evaporated to dryness. The dry crude residue was incubated at 80° C. for 30 minutes with 250 μL of N-methyl-N-trimethylsilyl trifluoroacetamide (MSTFA) to convert codeine and its transformation products to trimethylsilyl derivatives. The resulting products (0.5μL) were then injected onto a 10 meter, Series 530μ, 50% phenyl-methyl silicone column produced by Hewlett-Packard. The temperature of the column was maintained at 150° C. for 10 minutes, and then the temperature was increased 10° C. per minute until it reached 235° C. where it was kept for an additional 8 minutes. Injector and detector temperatures were 265° C. and 300° C., respectively. Helium, to act as the carrier, was supplied at 10 mL per minute. The amount of the various products was determined by comparing the retention times on the column and the areas of the peaks with those of known amounts of known standard compounds.

2. Analysis by high pressure liquid chromatography (HPLC):

The culture samples (10 mL) were centrifuged at 8,000 x g and samples of the resulting supernatant fluids (25 μL) were injected onto a 4.6 mm by 25 cm Zorbax ™ Sil column, manufactured by E. I. Du Pont De Nemours and Co. (Inc.), at 40° C. using a mixture of 0.13 N $NH_4OH$/MeOH (65%) and 0.13 N $NH_4OH$/$H_2O$ (35%) as the mobile phase. Detection of compounds was by ultraviolet absorbance. The compounds were quantitated by comparing the areas of the peaks with those resulting from the use of known amounts of known standard compounds.

EXAMPLE 1

An inoculum (1.25 mL) of *Streptomyces griseus* NRRL B8090 from a first stage culture was added to 50 mL of SFM in a 250 mL Erlenmeyer flask. The culture was incubated at 30° C. with shaking at 250 rpm. Twenty two and one-half hours later, 0.2 mL of a 10% solution of codeine phosphate was added to the culture. The cultures were further incubated at 30° C. with shaking at 250 rpm until 10 mL samples were removed 11 and 18 days later. The samples were analyzed by gas chromatography as described above to determine the quantities of codeine remaining and the amounts of 14-hydroxycodeine and norcodeine. The concentrations of 14-hydroxycodeine in the medium of the culture 10 and 17 days after the addition of codeine were 175 $\mu$M and 306 $\mu$M, respectively. The concentrations of norcodeine in the culture at the two time intervals were 25.9 $\mu$M and 52.2 $\mu$M, respectively.

EXAMPLE 2

This experiment was done essentially the same as Example 1 except the bacteria used were *Streptomyces griseus* ATCC 10137. The concentrations of 14-hydroxycodeine in the medium of the culture 10 and 17 days after the addition of codeine were 44.4 $\mu$M and 105 $\mu$M, respectively. The concentrations of norcodeine in the culture at the two time intervals were 41 $\mu$M and 139 $\mu$M, respectively.

EXAMPLES 3-10

A single experiment provides examples 3-10. The experiment was done essentially the same as Example 1 except that each culture contained different bacteria. Also, the samples removed for analysis were removed 14 days after the codeine was added in Examples 3-7 and 15 days after the codeine was added in Examples 8-10. The concentrations of 14-hydroxycodeine and norcodeine are given below.

| Example | Organism | Concentration, $\mu$M | |
|---|---|---|---|
| | | 14-hydroxy-codeine | norcodeine |
| 3 | *S. griseus* ATCC 23337 | 209 | <5 |
| 4 | *S. griseolus* ATCC 3325 | 148 | <5 |
| 5 | *S. species* WH110 | 12 | 25 |
| 6 | *S. griseolus* ATCC 11796 | 22 | 26 |
| 7 | *S. griseus* ATCC 13968 | 75 | 58 |
| 8 | *S. griseus* ATCC 21897 | 55 | 57 |
| 9 | *S. lincolnensis* ATCC 25466 | 118 | 29 |
| 10 | *S. punipalus* NRRL 3529 | 142 | 6 |

EXAMPLE 11

This experiment was designed to determine whether yeast malt-extract plus L-tyrosine medium or soybean flour medium would support the best yield of 14-hydroxycodeine from the transformation of codeine. The experiment was done essentially as in Example 1 except that flasks containing SFM and YMT media were each inoculated with either *S. griseus* NRRL B8090 or *S. griseus* ATCC 10137. The concentrations of 14-hydroxycodeine and norcodeine in the cultures were determined 17 days after codeine was added to the cultures. Results:

| Organism | Medium | Concentration ($\mu$M) | |
|---|---|---|---|
| | | 14-hydroxycodeine | Norcodeine |
| NRRL B8090 | SFM | 306 | 52.2 |
| NRRL B8090 | YMT | 92.1 | 30.7 |
| ATCC 10137 | SFM | 105 | 139.7 |
| ATCC 10137 | YMT | 79.5 | 62.3 |

The results show that *S. griseus* NRRL B8090 produced 3.3 times more 14-hydroxycodeine in SFM medium than in YMT medium and *S. griseus* ATCC 10137 produced 1.3 times more 14-hydroxycodeine in SFM medium that in YMT medium.

EXAMPLE 12

The experiments of this example were done essentially as that of Example 11. They differ prmarily in that YM medium was also included and the samples were collected 14 days after codeine was added to the cultures. Results:

| Organism | Medium | Concentration ($\mu$M) | |
|---|---|---|---|
| | | 14-hydroxycodeine | Norcodeine |
| NRRL B8090 | YM | 90 | 10 |
| NRRL B8090 | YMT | 80 | 20 |
| NRRL B8090 | SFM | 220 | 18 |
| ATCC 10137 | YM | 40 | 70 |
| ATCC 10137 | YMT | 70 | 30 |
| ATCC 10137 | SFM | 120 | 20 |

The results show that *S. griseus* NRRL B8090 produced more 14-hydroxycodeine than *S. griseus* ATCC 10137, that more 14-hydroxycodeine was produced in Soybean flour medium (SFM) and that the increased yield of 14-hydroxycodeine was obtained without a concomitant significant increase in norcodeine.

EXAMPLE 13

This experiment was designed to determine the optimum time to incubate the bacterial culture containing codeine. An inoculum consisting of 2.5 mL of a a first stage culture of *S. griseus* NRRL B8090 was added to 500 mL of SFM medium. The culture was grown overnight at 30° C. on a gyratory shaker. The next morning, a sufficient amount of a solution of codeine phosphate was added to bring the concentration of codeine in the culture to 1 mM. The culture was incubated further as before. Samples (10 mL) were removed each day for the first week and every 2 to 4 days thereafter until the 29th day. The samples were analyzed for their content of codeine, 14-hydroxycodeine and norcodeine.

Results:

The concentration of codeine decreased from day one throughout the period of culture, reaching a final concentration of 125 $\mu$M. The product, 14-hydroxycodeine, was first detected on the fifth day of culture. The concentration increased continually becoming nearly maximal on day 18 at a concentration of 217 $\mu$M (maximal concentration was 220 $\mu$M on day 21). The concentration remained essentially constant thereafter until the end of the experiment on day 30. Norcodeine was detected after the first day of culture. It reached its maximum concentration of 28 $\mu$M on day 5 and thereafter decreased until there was none in the culture at day 25.

The optimum time for the production of 14-hydroxycodeine in this culture was 18-20 days when maximal 14-hydroxycodeine had been produced but not all the codeine had been metabolized thus making it recoverable. These results are shown in the drawing.

EXAMPLE 14

This experiment was essentially the same as Example 13 except that the beginning concentration of codeine added to the culture was 2mM instead of 1 mM.

Results:

The product 14-hydroxycodeine was first detected on day 3 after the addition of codeine. It reached its maximum concentration of about 260 μM after 12 days of culture. As in the previous experiment the concentration of 14-hydroxycodeine stayed nearly constant thereafter while the concentration of codeine in the medium continued to decrease. Thus, the optimum time to get the maximum production of 14-hydroxycodeine and preserve the untransformed codeine would be after a 12 day culture period. As in Example 13, norcodeine production began immediately, reached a maximal concentration of about 57 μM on day 7 and decreased to undetectable levels by day 25.

EXAMPLE 15

This experiment was done to determine the optimum concentration of codeine to use. The bacteria used were *S. griseus* ATCC 10137 and the medium was either YM or YMT. Each culture contained 10 mL of medium that had been inoculated with 0.25 mL of a first stage culture. The resulting cultures were incubated overnight at 30° C. with continuous shaking at 250 rpm. Codeine as a solution of codeine phosphate was added to each culture so that one culture in each medium contained 1.25 mM, 2.5 mM, 5 mM, and 12.6 mM codeine. The cultures were incubated further, with shaking, for 7 days. Cell viability and the concentration of 14-hydroxycodeine were determined.

Results:

The number of viable cells dropped dramatically in those cultures containing codeine at a concentration of 12.6 mM. There was a greater number of viable cells in the cultures in YMT medium. Cells grown in YM medium produced more 14-hydroxycodeine when the starting concentration of codeine was 2.5 mM and none when the codeine concentration was 12.6 mM. Cells grown in YMT medium produced more 14-hydroxycodeine when the starting codeine concentration was 1.25 mM, less when the starting concentration of codeine was 2.5 mM and 5.0 mM, and none when the starting concentration of codeine was 12.6 mM. This is shown below.

| Medium | Starting codeine concentration (mM) | 14-hydroxycodeine concentration (μM) |
|---|---|---|
| YM | 1.2 | 24 |
|  | 2.5 | 46 |
|  | 5.0 | 32 |
|  | 12.6 | 0 |
| YMT | 1.2 | 62 |
|  | 2.5 | 21 |
|  | 5.0 | 23 |
|  | 12.5 | 0 |

What is claimed is:

1. A process for preparing 14-hydroxycodeine which comprises: contacting codeine or a water-soluble salt thereof with bacteria of the genus Streptomyces for a period of at least about three days while said bacteria are being aerobically cultured in a rich medium in which the growth nutrients are supplied in excess; and recovering 14-hydroxycodeine from the medium.

2. The process of claim 1 wherein the bacteria are *S. griseus*.

3. The process of claim 2 wherein the bacteria are *S. griseus* NRRL B8090.

4. The process of claim 1 wherein the rich medium is selected from the group consisting of soybean flour medium, yeast malt-extract medium, and yeast salt-extract medium with L-tyrosine.

5. The process of claim 1 wherein the rich medium is soybean flour medium.

6. The process of claim 1 wherein the concentration of codeine in the rich medium is less than about 5mM.

7. The process of claim 1 wherein the concentration of codeine in the rich medium is less than about 2.5mM.

8. The process of claim 1 wherein the contacting is carried out for a period of from about 3 to 30 days.

9. The process of claim 1 wherein the contacting is carried out for a period of from about 10 to 20 days.

10. A process for preparing 14-hydroxycodeine which comprises: contacting codeine or a water-soluble salt thereof with Streptomyces griseus bacteria for a period of about 3 to 30 days while said bacteria are being aerobically cultured in a rich medium in which the growth nutrients are supplied in excess and selected from the group consisting of soybean flour medium, yeast malt-extract medium, and yeast malt-extract medium with L-tyrosine; the codeine being present in the rich medium at a concentration less than about 5mM; and recovering 14-hydroxycodeine from the medium.

11. The process of claim 10 wherein the rich medium is soybean flour medium.

12. The process of claim 11 wherein the codeine concentration in the medium is less than about 2.5mM.

13. The process of claim 12 wherein the bacteria are *S. griseus* NRRL B8090.

14. A process for producing 14-hydroxycodeine which comprises: culturing a micro-organism belonging to the species *Steptomyces griseus, Streptomyces griseolus, Streptomyces punipalus,* or *Streptomyces lincolnensis* having the ability to produce said 14-hydroxycodeine in a nutrient medium in which the growth nutrients are supplied in excess and accumulating said 14-hydroxycodeine in said medium.

15. A process according to claim 14 wherein said micro-organism is selected from the group consisting of *S. griseus* NRRL B8090, *S. griseus* ATCC 10137, *S. griseus* ATCC 23337, *S. griseus* ATCC 13968, *S. griseus* ATCC 21897, *S. griseolus* ATCC 3325, *S. griseolus* ATCC 11796, *S. punipalus* NRRL 3529, *S. lincolnensis* ATCC 25466, and *S. species* WH110.

* * * * *